Figure 1:
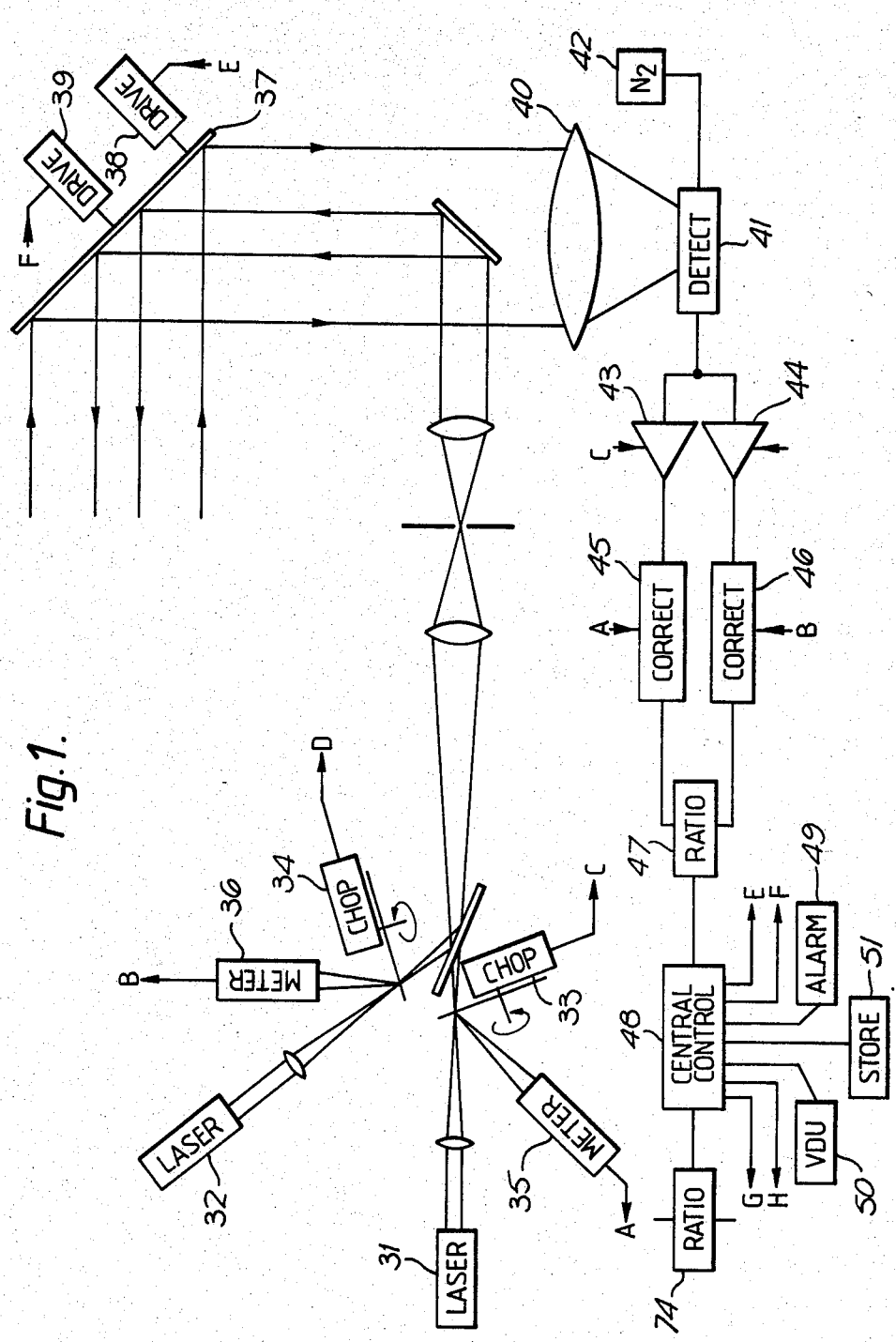

United States Patent [19]

Cramp

[11] Patent Number: 4,529,317

[45] Date of Patent: Jul. 16, 1985

[54] METHOD OF AND APPARATUS FOR MONITORING GASEOUS POLLUTANTS

[75] Inventor: John H. W. Cramp, St. Helens, England

[73] Assignee: Imperial Chemical Industries, PLC, London, England

[21] Appl. No.: 353,938

[22] Filed: Mar. 2, 1982

[30] Foreign Application Priority Data

Mar. 5, 1981 [GB] United Kingdom ................ 8106972

[51] Int. Cl.$^3$ ........................................... G01N 21/35
[52] U.S. Cl. ..................................... 356/407; 356/51; 356/437; 250/338; 250/339
[58] Field of Search ................. 356/51, 407, 409, 437, 356/438, 342, 1; 250/205, 339, 343, 345, 338 GA; 340/632

[56] References Cited

U.S. PATENT DOCUMENTS 3,766,380 10/1973 Menzies .......................... 356/438 X
3,998,557 12/1976 Javan .
4,426,640 1/1984 Becconsall et al. .................. 340/632

FOREIGN PATENT DOCUMENTS 2208559 8/1973 Fed. Rep. of Germany .
2607169 9/1977 Fed. Rep. of Germany .

OTHER PUBLICATIONS

Marthinsson et al., *Optical and Quantum Electronics,* vol. 12, No. 4, Jul. 1980, pp. 327–334.
Journal of Applied Physics, vol. 46, No. 7, Jul. 1975, W. B. Grant and R. D. Hake, Jr., pp. 3019–3023.
Optical Engineering, vol. 17, No. 6, Nov.–Dec. 1978, pp. 658–660.
Eagle–Elliott Absorption Gas Laser Equipment, GP–Elliott Electronic Systems Ltd., 4 pages.

*Primary Examiner*—F. L. Evans
*Attorney, Agent, or Firm*—Cushman, Darby & Cushman

[57] ABSTRACT

Laser scanning apparatus for monitoring gaseous pollutants uses two intersecting scanning beams so that the point of intersection (which is monitored by both scanning beams) can be identified by triangulation.

5 Claims, 3 Drawing Figures

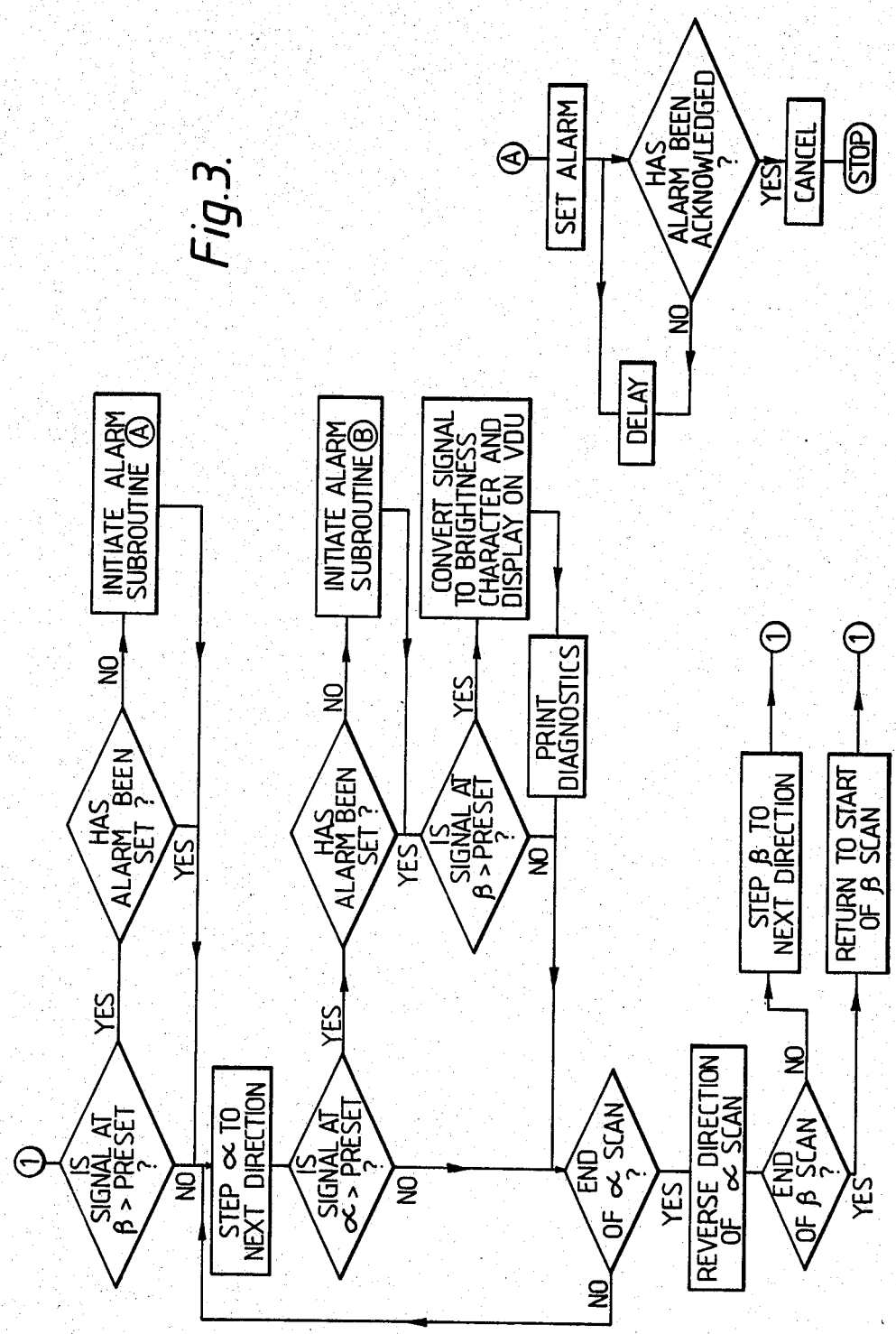

METHOD OF AND APPARATUS FOR MONITORING GASEOUS POLLUTANTS

The invention relates to the remote monitoring of one or more selected gases, especially pollutants in a gaseous environment.

In the specification of our copending European patent application No. 80302867.9 under the same title, (corresponding to U.S. Pat. No. 4,426,640 of Becconsall et al., issued Jan. 17, 1984) we describe a method for the remote quantitative monitoring of one or more selected gases in a gaseous environment, and also apparatus for carrying out such monitoring. The method described in that specification (which for simplicity may be referred to in this specification as "the method herein specified") comprises the steps of generating electromagnetic radiation from laser sources to give at least one detection beam containing a specific absorption wavelength of the gas or gases being monitored and at least one reference beam having a wavelength that is significantly less strongly absorbed by the gas or gases being monitored, modulating the amplitude of each of the beams with different modulation frequencies or phases, combining the modulated beams into a single beam in which the component modulated beams are substantially coincident with one another, displacing the combined beam angularly through the gaseous environment so as to direct the combined beam towards a plurality of locations sequentially and repetitively, collecting at least a portion of the radiation which is returned from each of the locations, deriving electrical signals corresponding to the intensity of the collected radiation, isolating the electrical signals corresponding to the intensity of the radiation having the aforesaid modulation frequencies or phases, and obtaining the ratio of the isolated signals corresponding to radiation collected from a detection beam and a related reference beam thereby to provide a measure of the amount of the selected gas or gases in each beam path traversed by the collected radiation originating from the laser sources.

The apparatus described in that European specification (which may similarly be referred to in this specification as "the apparatus herein specified") comprises laser sources for generating electromagnetic radiation capable of being tuned to give at least one detection beam containing a specific absorption wavelength of the gas or gases to be monitored and at least one reference beam having a wavelength that is significantly less strongly absorbed by the gas or gases to be monitored, means for modulating the amplitude of each of the beams with different modulation frequencies or phases, means for combining the modulated beams into a single combined beam in which the component modulated beams are substantially coincident with one another, scanning means to displace the combined beam angularly through the gaseous environment so as to direct the combined beam towards a plurality of locations sequentially and repetitively, means for collecting at least a portion of the radiation which is returned from each of the locations, a detector for deriving electrical signals corresponding to the intensity of the collected radiation, means for isolating the electrical signals corresponding to the intensity of radiation having the aforesaid modulation frequencies or phases, means for obtaining the ratio of the isolated signals corresponding to radiation collected from a detection beam and a related reference beam thereby to provide a measure of the amount of the selected gas or gases in each beam path traversed between the apparatus and the scanned locations, and means for indicating the amount of gas detected.

In that earlier specification, we described our prototype installation in which the apparatus was mounted on a tall tower overlooking a polyethylene plant but outside the hazard area. The beam was directed downwards as it scanned the area from the tower, and because of its elevated mounting, the position of any gas leak within the area could be accurately identified. However, we have now found that when monitoring gases over some large flat areas, the optimum height of the tower is inconveniently large.

According to a first aspect of the present invention, there is provided a method for the remote quantitative monitoring of one or more selected gases in a gaseous environment, which comprises the method herein specified characterised in that scanning beams, each comprising combined reference and detection beams, are directed towards the locations from two spaced-apart scanning positions such that each scanning beam passes through a plurality of locations, and the ratio signals providing a measure of the amount of absorbing gas in each scanning beam are correlated to provide a measure of the amount of gas at each location identified as the point of intersection of the two beams.

The point of intersection of the two scanning beams is readily determined by simple triangulation. For example, this can be done graphically (e.g. using a VDU display or printer) or by solving the equation:

$$R = d \frac{\sin \beta}{\sin (\alpha + \beta)}$$

where R is the range to the location X from one scanning means at a point A, d is the known distance from A to the other scanning means at a point B, and $\alpha$ and $\beta$ are the internal angles at A and B respectively of the triangle ABX, i.e. the angles of the scanning beams to the line interconnecting the scanning positions.

Where the gas leaks and remains as a narrow plume, a measure of both gas plume location and quantity of gas at that location, can be obtained with considerable accuracy, although for a plume extending in line with one of the scanning beams, several scans to obtain the direction of plume growth may be required in order to determine at which end of the plume the originating leak is located. However, in practice wind eddies and continuance of the gas leakage, generally diffuse the plume of gas into a larger irregular shape, and with only two scanning beams the measure of the quantity of leaked gas at any specific location becomes increasingly inaccurate. The accuracy can be increased to a limited extent by adding further scanning beams to scan the area from other scanning positions, but for situations where the main objective is to detect leaks and to determine where they occur, the inaccuracies of quantitative measurement may be of little importance since the only quantitative measurement required is a distinction between an uncharacteristically high level and a normally zero or insignificantly low concentration. For gas at high pressure, such changes tend to occur very abruptly. It is the sensitivity of the present invention enabling it to detect such changes very quickly and with certainty (rather than to measure accurately the precise amount of escaped gas and its ability to identify the location or regions of leaking gas within what may be a large scanned area, which we find renders it particularly useful for monitoring gas leaks.

A preferred process is therefore one which comprises comparing the ratio signals providing the measure of the amount of gas detected by each of the two scanning beams, with preset threshold signals representing a tolerable level of gas, and providing an indication, e.g. by setting an alarm or displaying on a VDU or locations indicating matrix display (as described hereinafter), whenever the ratio signal for one or both of the scanning beams exceeds the threshold signal with which is is compared.

Under some circumstances, e.g. where the scanning positions are such that under prevailing wind conditions one scanning beam would travel longitudinally along any gas plume while the other would intersect it transversely, it can be advantageous to use different threshold levels for the two scanning beams. However, wind directions generally vary and wide angle scanning leads to different plume/beam angles, so for most applications it is preferred to use the same threshold levels for both scanning beams, and indeed also for any additional beams which may be used to obtain further information.

A leak is detected when just one, either one, of the ratio signals exceeds the threshold signal. In order that the presence of a leak may be apparent as early as possible, we prefer that an indication (e.g. an alarm) be provided whenever the threshold signal is exceeded in respect of either of the two scanning beams, as the leaked gas will usually not intercept both beams simultaneously whatever the manner of scanning employed. Identification of the leaking locations can then be treated as a separate issue once the alarm has been raised at the earliest opportunity.

In order to locate the position of a leak, the area can be scanned by the two beams in a number of ways. Each beam passes through a number of locations, and if the two beams merely moved synchronously in opposite directions, the beams would simply intersect along their median line within the plane of scan. To overcome this problem, one option comprises scanning each beam independently through sectors of circles subtended by the scanning positions, on detecting a leak identifying for each beam in which scanned sectors the threshold signal is exceeded, and determining the regions for which those identified sectors overlap, thereby providing an indication of the locations in which the escaped gas has been identified. The beam would usually be scanned smoothly through adjacent sectors, but this method is also equally applicable where the beam is jumped from one to another of spaced sectors which can be as narrow as the divergence angles of the scanning beams should the circumstances warrant it. A second option is to adjust the rates of scan of the two beams so that they intersect in all locations in turn, and provide an indication for each location in which the beams intersect whenever the threshold signal is exceeded in both beams simultaneously. As will be appreciated, this can occur when both beams travel through a cloud of gas to intersect in a gas free location beyond the cloud. Indicating gas in locations free from gas is the principle error to which we referred above, but all locations containing gas in the threshold exceeding quantities should be indicated.

The former option of independent scanning requires some form of memory, e.g. a paper chart, magnetic disc, computer memory store (RAM) or VDU screen with extended image retention, although it is not always necessary to use the memory all the time. Thus for example, each beam scans the area independently until a leak occurs, and then each will detect that the threshold is exceeded in a sector of a circle subtended by the scanning position. The two sensors may have different internal angles, but the areas common to both sectors give the location of the gas. The identity of these sectors may be held numerically in a data base or shown graphically on a VDU or other form of visual display, or the common areas can just be calculated, and only those common areas indicated. A variation is to scan alternately with each of the two beams, so that each beam only scans for half the total monitoring period. A further variation is to scan with only one beam until a gas leak is detected, merely using the other beam to determine the affected area.

The second option, in which the scanning rates are interrelated so as to scan each location in turn with the two beams together, can also be carried out in various ways. One way is to scan the area with both beams simultaneously so that their intersection traverse, the area, the relative phase of the two scans being adjusted at the end of each traverse so that the intersection passes through a different set of locations in subsequent traversals of the area. An alternative method is one which comprises scanning the two beams at different rates, the faster-scanning beam traversing the area a plurality of times for each single traverse of the slower-scanning beam such that the point of intersection of the two beams passes through all the locations wherein the gas is to be monitored, during each traverse of the slower-scanning beam. It is preferred that the slower-scanning beam be traversed stepwise, each step occurring at one end of each traverse by the faster-scanning beam. Alternate traverses by the faster-scanning beam are then preferably in opposite directions so that with the slower- scanning beam in one position, the faster-scanning beam scans the area in one direction so that the point of intersection passes through all the locations in the slower-scanning beam. The latter then moves on one step so that as the faster-scanning beam traverses the area in the reverse direction, and the point of intersection of the two beams passes through a further set of locations.

According to a further aspect of the present invention, there is provided an apparatus for the remote quantitative monitoring of one or more elected gases in a gaseous environment, which comprises the apparatus herein specified characterised by having two spaced-apart scanning means, each being aligned for directing a scanning beam comprising combined reference and detection beams towards each of the locations; and means for correlating the ratio signals derived from the two scanning beams thereby to provide a measure of the amount of gas at each location identified as a point of intersection of the two beams.

We prefer to provide each scanning means with beam-producing equipment comprising laser sources, modulating means and means for combining the modulated beams, which is separate from the beam-producing equipment of the other scanning means. An alternative is to use a single beam-producing equipment and to split the beam, either temporally or spatially; but under plant conditions, where vibrations and other movements can affect alignment between a single split source and remote scanning mirrors (which can be located a substantial distance apart on large plant areas), the use of separate beam-producing equipment for the two scanning positions is generally preferred.

Apparatus that is quick and convenient to use comprisesa locations indicating matrix display wherein the locations being monitored are each represented by a separate indicating means (e.g. light bulb, LED or flag) connected to function when both beams produce a signal greater than its threshold signal when they pass through the location which that indicating means represents. This enables the region of any leakage to be identified at a glance. When using synchronised scans, the matrix can be operated by feeding the signal from each beam to the indicator means via an AND gate. Where the beams scan independently, a simple go/no go signal signifying above or below the threshold respectively can be provided for each beam direction. This will be the signal for a whole row of locations, each of which will have a different angle for the other beam. The signals for each direction in turn are then updated each time the beam sweeps its full course, and while they are held they provide an enable state with which the other beam's signals are compared in turn. When using computer control a O or I state (representing above or below the threshold) can be applied to a whole row of addresses in the computer memory representing all the locations in the beam at that one time. After scanning through all the locations, and applying the appropriate state to each row of addresses in turn, the process is repeated and the states up-dated as necessary. Similarly for the other beam. When any location becomes represented by two above-the-threshold states, the relevant location indicator is operated in the matrix display.

A particularly versatile apparatus is one which combines an ability to be able to indicate variations in the leaked gas concentration, rather than that it is (or is not) greater than some threshold level, yet which also provides an alarm. Such an apparatus comprises alarm means operable when the ratio signal of either beam exceeds the threshold signal, and means to indicate the amount of the selected gas as measured for each location. Indicating the measured amount of gas, e.g. in terms of relative brightness on a VDU screen, rather than simply whether or not it exceeds the threshold value, can help a skilled operator locate the source of the gas within the detected cloud.

Figure 2:
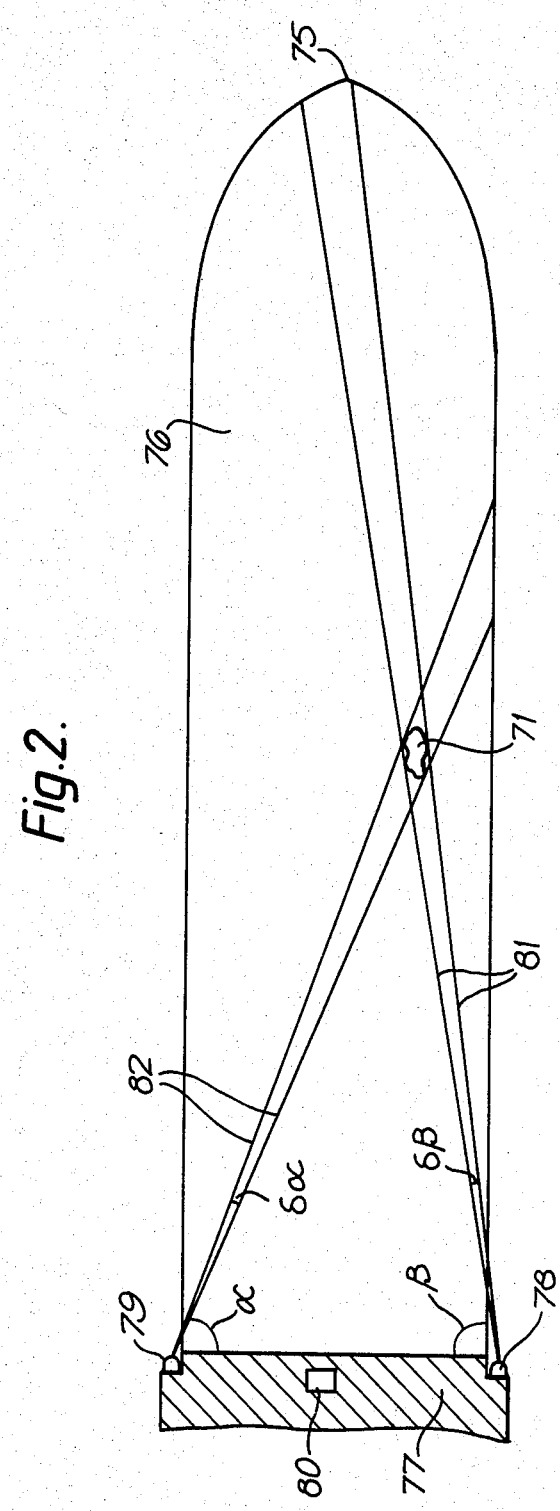

The invention is illustrated by reference to a specific embodiment thereof, shown in the accompanying drawings, of which:

FIG. 1 is a block diagram of part of an apparatus for monitoring methane in the atmosphere immediately above the deck of a supertanker for carrying crude oil or petroleum products, FIG. 2 is an illustration of the apparatus in use, and FIG. 3 shows the principle features of the logic used in controlling the apparatus.

The apparatus comprises two special scanning means coordinated by a central control unit with associated gas indicators. Each scanning means together with the central computer, is basically similar to that shown in FIG. 2 of the aforesaid European specification, although different lasers are used. The beam handling device shown in FIG. 1 comprises two continuous-mode helium-neon lasers 31, 32 providing respectively a detection beam at 3.39 μm (which is absorbed by methane) and a non-absorbed reference beam at a nearby wavelength obtained by including a cell of methane gas in the optical cavity of the laser. The detection and reference beams are passed through choppers 33, 34 with light reflected from the back of the chopper blades being directed to power meters 35, 36. The power meters 35, 36 continuously monitor the power output of the lasers 31, 32 and give out signals A and B which are a measure of the laser power. The choppers also give out signals C and D indicative of their rates of rotation and hence of the frequencies at which the respective beams are being chopped. After modulation by the choppers, the beams are combined using a slab of zinc selenide set at the Brewster angle.

The scanning means is a mirror 37 whose orientation is controlled by two drive motors 38, 39 which tilt the mirror about two perpendicular axes. The combined beam impinges on the mirror, and is reflected towards the various locations in turn by movement of the mirror. The two drive motors are controlled by signals $\beta_1$ and $\beta_2$ respectively.

A small fraction of the radiation directed at the various locations is scattered back in the direction of the apparatus by the deck, pipes and bulwarks of the vessel; and is reflected by the mirror 37 onto a lens 40, which focusses the light directly onto a liquid nitrogen cooled detector 41, having automatic topping-up means 42 for the cooling liquid. The output from the detector is divided and fed to two lock-in amplifiers 43, 44 taking signals C and D from the choppers to provide a continuous reference for the lock-in frequency. These amplifiers isolate the two modulated signals, which are smoothed and then corrected for power fluctuations in their respective originating lasers, by ratiometers 45, 46 using signals A and B from the power meters as their references. The corrected signals (which represent the returned fractions of the detection and reference beams, modified by absorption of the detection beam by any methane through which the beam passes, either before or after it is scattered back towards the apparatus) are then compared in a further ratiometer 47, and the ratio obtained is fed to a computer 48 as the central control unit, the various functions of which will be described hereinafter.

Also connected to the computer is a second beam handling device, spaced apart from that shown in FIG. 1, but duplicating it, having a pair of lasers for providing detection and reference beams, modulating choppers, scanning mirror, detector and lock-in amplifiers for separating the signals representing the returned portions of the detection and reference beams, and being connected to the computer 48 via a ratiometer 74 equivalent to that 47 of the first device. The computer 48 is connected to a visual display unit 50, a store 51 and an alarm 49. It also provides control signals E and F for the drive motors 38, 39 and corresponding signals G and H for the drive motors of the duplicate part of the apparatus which is not shown in the drawing.

The installation of the apparatus is shown in FIG. 2, which shows part of the supertanker (somewhat foreshortened), including the bows 75, deck 76 and bridge 77. Mounted near the outer ends of the bridge are the two beam handling devices 78, 79 described above. These are connected to a central control unit 80 mounted in the bridge with its attendant VDU 50, store 51 and alarm 49. The beam-handling devices direct a beam almost parallel to the deck, the scanning mirrors causing the two beams to scan through angles of $\alpha$ and $\beta$ respectively which vary approximately from 0° (across the ship parallel to the bridge) to 90° (parallel to the centre line of the ship). In the drawing there has also been shown a cloud of methane 71, which subtends angles of $\delta\alpha$ and $\delta\beta$ respectively at the two beam-handling devices, at the instant depicted.

The monitoring operation is controlled by the computer, and the basic logic steps are shown in FIG. 3. With the starboard scanning device 78 directing its scanning beam 81 across the deck at an angle $\beta_1$, the port scanning device 79 directs its scanning beam 82 across the deck at an angle $\alpha_1$, which intersects the starboard beam at a specific location above the deck. By control signals G, H, from the computer to the port mirror drives, the port beam scans across the deck through varying angles $\alpha$, such that the point of intersection moves along the length of the starboard beam while the latter remains at the same angle $\beta_1$. For control purposes this is taken in small discrete steps, but the time interval is so small that in practice the full length of the starboard beam is scanned in a single smooth movement. When the whole length of the starboard beam has been scanned, the computer sends out signals E and F to step the mirror to a new position giving a new beam direction of $\beta_2$. The port beam is then scanned in the reverse direction, back along the whole length of the starboard beam. This is continued for all values of $\beta$ to cause the point of intersection of the two scanning beams to pass through all locations above the deck area where monitoring is required.

In order for portions of the scanning beams to be returned to their respective detectors, it is necessary for them to impinge on something which will scatter the radiation, or (more rarely) to reflect it back to the beam handling device from which it originated. This is accomplished by a slight downwards inclination of the two scanning beams so that they impinge on the deck or bulwarks, and by providing panels of radiation-scattering material along the gunwales where necessary (e.g. towards the bridge), in order to maintain the beam angles near to the horizontal, thereby to enable the simple scanning logic of FIG. 3 to be used. An alternative is to use beams inclined to the horizontal e.g. so that they may be scattered by the deck without needing radiation-scattering panels to be provided, and to vary the angles of inclination as one beam scans along the length of the other.

In the event of a leak occurring, the cloud of gas could be detected by either beam first, so the alarm is set by the central control whenever either of the detectors receives a returned scanning beam which has passed through the cloud. When such a beam is collected, the signal from the ratiometer (47 or 74 as the case may be) differs from unity by an amount representative of the amount of absorption of the detection beam by the gas, and is compared by the computer with a preset tolerable limit. If it is greater, the computer sets the alarm (if not previously set). It also prints the diagnostic (e.g. date, time, $\alpha$, $\beta$ and signal) whenever both scanning beams detect gas.

The main scanning routine continues, and thus provides a record of the growth of the gas cloud. No matter which scanning beam first intercepts the gas cloud, both will do so eventually, and as shown in the example in FIG. 2, the position of the cloud will be identified as being in the area of intercept between the sector of angles $\beta$ to $(\beta+\delta\beta)$ and the sector of angles $\alpha$ to $(\alpha+\delta\alpha)$. The VDU carries a plan of the ship, and when both scanning beams indicate that gas is present, the signal is converted to a brightness character which is displayed on the VDU.

Thus the alarm sequence is triggered as soon as gas is detected, and is maintained until acknowledged and the position of the gas cloud is progressively built up on the VDU screen as the information is obtained, and as the shape of the cloud develops as the leak continues.

This is one application which can improve security, particularly while the ship is loading or unloading or following severe weather which may have caused unapparent damage. Variations include the use of carbon dioxide lasers for detecting ethylene and other gases, and the combination of a rapid-scanning starboard beam with a slow-scanning port beam. Indeed security means comprising apparatus as described herein is particularly suitable for use on a variety of different kinds of ships for carrying the selected gases or materials from which the selected gases can escape, e.g. by evaporation, decomposition, dissolution of soluble gases from their solutions or simply by separation of gases entrained in liquids, such as crude oil. In each case the apparatus is mounted to scan once over the carrying means from two spaced apart positions on the ship, e.g. as shown in FIG. 2.

What we claim is:

1. A method for the remote quantitive monitoring of one or more selected gases in a gaseous environment, which comprises the steps of generating electromagnetic radiation from laser sources to give at least one detection beam containing a specific absorption wavelength of the gas or gases being monitored and at least one reference beam having a wavelength that is significantly less strongly absorbed by the gas or gases being monitored, modulating the amplitude of each of the beams with different modulation frequencies or phases, combining the modulated beams to form scanning beams in each of which the component modulated beams are substantially coincident with one another, displacing the scanning beams angularly through the gaseous environment so as to sequentially and repetitively direct them towards a plurality of locations from two spaced-apart scanning positions, collecting at least a portion of the radiation from each scanning beam which is returned from each of the locations, deriving electrical signals corresponding to the intensity of the collected radiation, isolating the electrical signals corresponding to the intensity of the radiation having the aforesaid modulation frequencies or phases, obtaining the ratio of the isolated signals corresponding to radiation collected from a detection beam and a related reference beam thereby to provide a measure of the amount of the selected gas or gases in each beam path traversed by the collected radiation originating from each of the spaced scanning positions, and correlating the ratio signals derived from the two scanning beams to provide a measure of the amount of gas at each location identified as the point of intersection of the two scanning beams.

2. A method as claimed in claim 1 which comprises comparing the ratio signals providing the measure of the amount of gas detected by each of the two scanning beams, with preset threshold signals representing a tolerable level of gas, and providing an indication whenever the ratio signal for one or both of the scanning beams exceeds the threshold signal with which it is compared.

3. A method as claimed in claim 2 wherein an indication is provided whenever a threshold signal is exceeded in respect of either of the two scanning beams.

4. A method as claimed in claim 2 or claim 3 which comprises scanning each beam independently through sectors of circles subtended by the scanning positions, on detecting a leak identifying for each beam in which scanned sectors the threshold signal is exceeded, and determining the regions for which those identified sectors overlap, thereby providing an indication of the locations in which the escaped gas has been identified.

5. A method as claimed in claim 2 or claim 3 which comprises adjusting the rates of scan of the two beams so that they intersect at each location in turn, and providing an indication for each location in which the beams intersect when the threshold signal is exceeded for both beams simultaneously.

* * * * *